US009995657B2

(12) United States Patent
Hu et al.

(10) Patent No.: US 9,995,657 B2
(45) Date of Patent: Jun. 12, 2018

(54) TEST DEVICE FOR FLUID SPECIMENS

(71) Applicant: ABON BIOHPARM (HANGZHOU) CO., LTD, Hangzhou (CN)

(72) Inventors: Lin Hu, Hangzhou (CN); Haipeng Hu, Hangzhou (CN); Yinfei Wu, Hangzhou (CN)

(73) Assignee: ABON BIOPHARM (HANGZHOU) CO., LTD, Zhejiang (CN)

( * ) Notice: Subject to any disclaimer, the term of this patent is extended or adjusted under 35 U.S.C. 154(b) by 503 days.

(21) Appl. No.: 14/435,681

(22) PCT Filed: Sep. 26, 2013

(86) PCT No.: PCT/CN2013/084273
§ 371 (c)(1),
(2) Date: Apr. 14, 2015

(87) PCT Pub. No.: WO2014/063553
PCT Pub. Date: May 1, 2014

(65) Prior Publication Data
US 2015/0268135 A1   Sep. 24, 2015

(30) Foreign Application Priority Data
Oct. 24, 2012   (CN) .......................... 2012 1 0409899

(51) Int. Cl.
*G01N 1/10* (2006.01)
*B01L 3/00* (2006.01)
(Continued)

(52) U.S. Cl.
CPC .............. *G01N 1/10* (2013.01); *A61B 10/007* (2013.01); *A61B 10/0045* (2013.01);
(Continued)

(58) Field of Classification Search
CPC .... G01N 1/10; G01N 33/48714; B01L 3/502; B01L 2400/0644; B01L 2300/0663;
(Continued)

(56) References Cited

U.S. PATENT DOCUMENTS

2009/0023270 A1   1/2009   Akiyama et al.

FOREIGN PATENT DOCUMENTS

| CN | 101581729 A | 11/2009 |
| CN | 202928839 U | 5/2013 |
| CN | 203083845 U | 7/2013 |

OTHER PUBLICATIONS

International Search Report and Written Opinion for PCT/CN2013/084273, dated Jan. 2, 2014 (Jan. 2, 2014); the whole document.

*Primary Examiner* — Peter Macchiarolo
*Assistant Examiner* — Anthony W Megna Fuentes
(74) *Attorney, Agent, or Firm* — Steptoe & Johnson LLP

(57) ABSTRACT

This invention is related to a device for collection and test of fluid specimens, comprising a first cavity and a second cavity; wherein, the first cavity is located inside the second cavity; furthermore, the first and second cavities are interconnected; the said first cavity is available for mutual rotation with the second cavity to facilitate fluid to flow between them; the first cavity is provided with a first position and a second position inside the second cavity. The device of this invention can ensure adequate and uniform mixing of fluid inside the second cavity to facilitate further tests.

18 Claims, 9 Drawing Sheets

Figure 1:
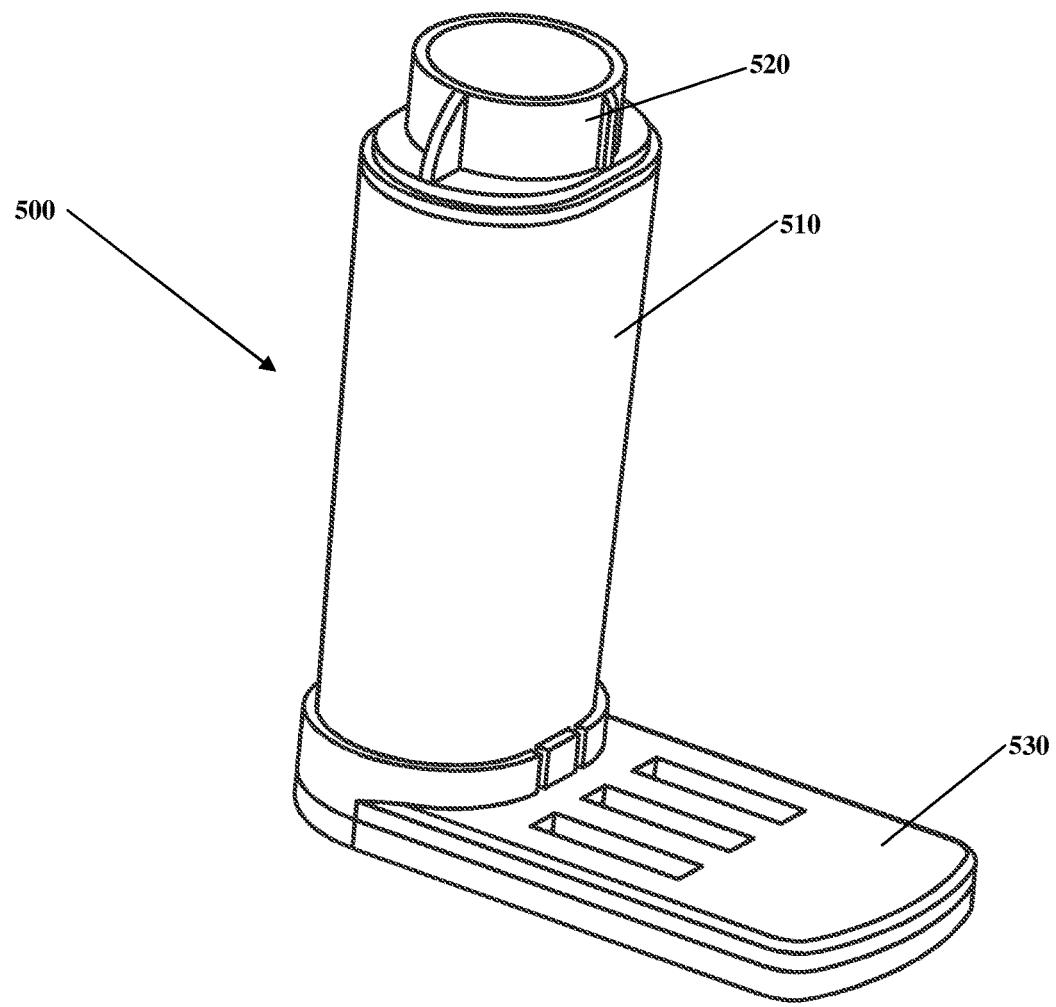

(51) Int. Cl.
*A61B 10/00* (2006.01)
*G01N 33/487* (2006.01)

(52) U.S. Cl.
CPC ........ B01L 3/502 (2013.01); G01N 33/48714 (2013.01); *A61B 10/0038* (2013.01); *A61B 10/0051* (2013.01); *A61B 2010/0006* (2013.01); *A61B 2010/0009* (2013.01); *A61B 2010/0074* (2013.01); *B01L 2200/027* (2013.01); *B01L 2300/0663* (2013.01); *B01L 2300/0672* (2013.01); *B01L 2400/0475* (2013.01); *B01L 2400/0481* (2013.01); *B01L 2400/0644* (2013.01); *B01L 2400/0683* (2013.01)

(58) Field of Classification Search
CPC ....... B01L 2200/027; B01L 2400/0683; B01L 2400/0481; B01L 2400/0475; B01L 2300/0672; A61B 10/0045; A61B 10/007; A61B 2010/0006; A61B 10/0051; A61B 2010/0009; A61B 10/0038; A61B 2010/0074
USPC .......................... 73/864.33, 864.83, 864.43; 422/68.1–82.03, 401, 405
See application file for complete search history.

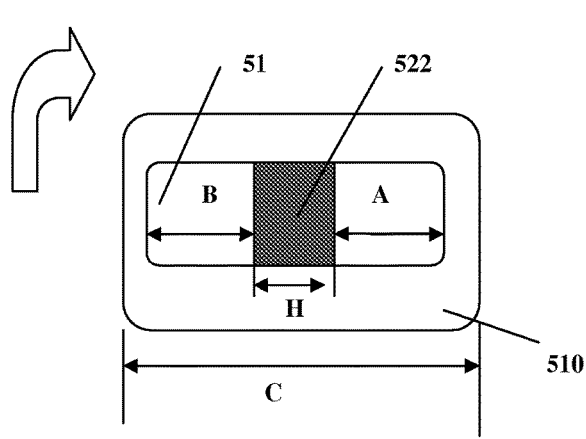
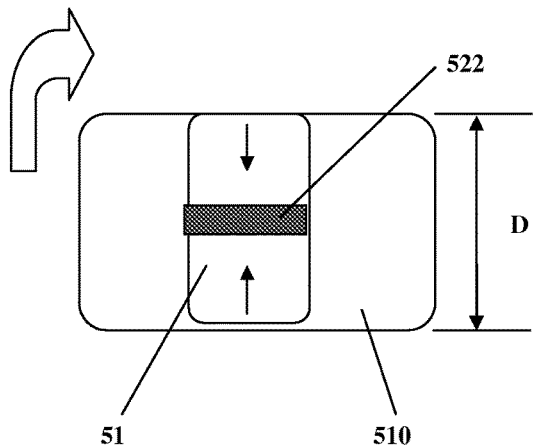
Fig.14A　　　　　　　　　　　Fig.14B
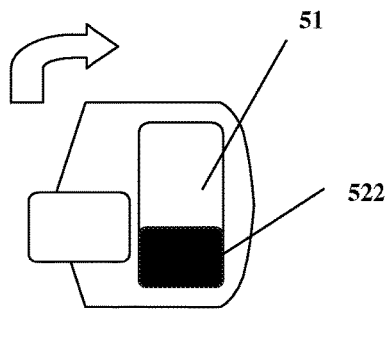
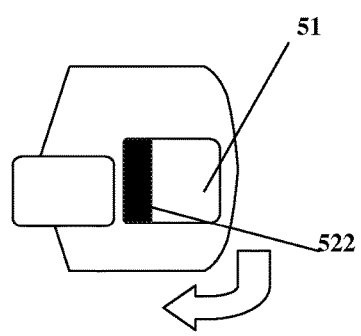
Fig.15A　　　　　　　　　　　Fig.15B

TEST DEVICE FOR FLUID SPECIMENS

CLAIM FOR PRIORITY

This application claims priority under 35 USC 371 to International Application No. PCT/CN2013/084273, filed Sep. 26, 2013, which claims priority to Chinese Patent Application No. 201210409899.3, filed Oct. 24, 2012, each of which is hereby incorporated by reference in its entirety.

FIELD OF THE INVENTION

This invention is related to a device, in particular to a device for collection and test of fluid specimens.

BACKGROUND

The following background arts are for easy comprehension of this invention by readers, which shall not be deemed as prior arts.

Drug abuse has become a recognized and deteriorated social problem in our society. According to survey by U.S. Department of Health and Human Services in 2003, 19.5 million or 8.2% U.S.A citizens over the age of 12 were taking illegal drugs. "The recently used illegal drug" refers to an illegal drug used one month prior to the survey by U.S. Department of Health and Human Services. As discovered, mariguana is the most common illegal drug with population proportion up to 6.2% (14.6 million). It is estimated that the number of people using cocaine, crack, psychedelic and heroine is up to 2.3 million (1.0%), 604,000, 1 million and 119,000 respectively.

Some other devices for collection of salvia and detection of illegal drug compositions are disclosed in US2004/0184954 and US2004/0237674. Devices and methods for collection and test of saliva are also provided in the two patents. In such devices, specimens in the absorption part of collector are to be extruded into the collection cavity for test under the external force imposed. However, some specimens may result in pollution or infection through contact with operator during coordinated extrusion by collection rod and cavity. Furthermore, such collection devices will be inconvenient for operation if specimens are to be mixed with buffer solution for test.

Therefore, it is necessary to provide optimal methods and devices for collection and test of specimens.

SUMMARY OF THE INVENTION

The new device of this invention can ensure adequate mixing of specimens and buffer solution to facilitate further tests.

In one aspect, this invention aims to provide a device, comprising a first cavity and a second cavity; wherein, the first cavity is located inside the second cavity for interconnection; the said first cavity and the second cavity are available for corresponding movement to facilitate fluid to flow between them.

In a preferred embodiment, the first cavity is interconnected with the second cavity; in other words, fluid is available for flow or transfer between the first cavity and the second cavity. The first cavity comprises an opening for interconnection of the first cavity and the second cavity, from which the fluid flows into the second cavity.

In some preferred embodiments, the first cavity is provided with a position1 and a second position inside the second cavity.

In some further preferred embodiment, volume of the first cavity rotated to the second position from first position in correspondence to the second cavity is to be reduced to facilitate fluid inside it to flow into the second cavity.

In some preferred embodiments, fluid inside the first cavity will flow into the second cavity when the space or volume of the first cavity is changing. In some embodiments, fluid inside the first cavity will irreversibly flow into the second cavity when the space or volume of the first cavity is changing.

In some preferred embodiments, variation to the space and/or volume of the first cavity is represented by reduction in volume and/or space.

In some preferred embodiments, space of the first cavity is to be narrowed when it rotates to from first position to second position in correspondence to the second cavity to facilitate fluid inside the first cavity to flow into the second cavity; alternatively, space of the first cavity rotating from second position to first position is to be recovered; in other words, fluid can also flow from the second cavity into the first one when the first cavity is at first position.

In some preferred embodiments, the first cavity is interconnected with phase fluid inside the second cavity via the open side wall or opening on its wall. In some further embodiments, the device also comprises a moving element, such as slot; the moving element matches the opening on the connected wall, which can move inside the first cavity to reduce its volume. In a preferred embodiment, the moving element is located inside the first cavity. In some embodiment, the moving element is to depart from the first cavity located at first position in correspondence to the second cavity; the moving element is to approach or enter the first cavity to extrude or enter the first cavity to change (reduce) its volume when it moves in correspondence to the second cavity; fluid inside the first cavity will flow into the second cavity from the first one once the volume is changed. In some embodiments, one part of moving slot is located inside the opening on the wall of the first cavity; whereas another one is in contact with inner wall of the second cavity; as a result of movement of the first cavity in correspondence to the second cavity, the slot will shift to the first cavity via the opening to reduce its volume.

In an embodiment, the moving element or slot is provided with a projection matching with the second cavity; when the first and second cavities are rotating, the second cavity will push the projection to make the moving element move into the first cavity to reduce its volume. In some embodiments, the first cavity comprises two symmetrical openings for interconnection with fluid inside the second cavity; correspondingly, the two symmetrical openings also comprise two symmetrical moving elements or slots. When the first cavity moves inside the second one, symmetrical moving elements will enter or extrude the first cavity to change or reduce its volume so as to make the fluid inside the first cavity flow into the second cavity. In some embodiments, such elastic elements as spring can be installed among symmetrical moving elements, such as spring; the space of slot is to be narrowed in the approaching process to reduce the volume of the first cavity or directly compress fluid specimen absorption carrier inside the first cavity; otherwise, it is applicable to increase the volume of the first cavity or reduce the compression frequency.

In some preferred embodiments, fluid specimens in the first cavity can be absorbed by extruding or compressible carrier; at normal status, fluid specimens are to be absorbed by the carrier other than flowing; fluid specimens are to be extruded out of the carrier under compression. In view of aforesaid embodiments, as the volume of the first cavity is changed, it is applicable to extrude carrier in it to make fluid specimens on the carrier flow into the second cavity via the reserved gap between the slot and the opening on the slot wall. In some preferred embodiments, the carrier carrying fluid specimens are to be extruded by the moving slot directly.

In some further embodiments, the device also comprises a collection rod composed of compressible carrier; the compressible carrier is used to absorb or collect fluid specimens. In some particular embodiments, the collection rod matches with the first cavity to ensure mutual rotation of the first and second cavities.

In particular embodiments, the moving element comprises a passage for fluid to flow into the second cavity from the first one. In other words, the slot is provided with a groove for fluid to flow into the second cavity from the first one.

In still a further embodiment, the slot is provided with clamping strip matching with the side wall of the first cavity.

In some further embodiments, the device also comprises a third cavity interconnected with the first cavity. In a preferred embodiment, the first cavity is fixed to the third one to ensure simultaneous movement of the first and third cavities. In a preferred embodiment, a poking element, such as a flake projection, is provided on the outer wall of the third cavity. In a further preferred embodiment, the flake projection is located at the symmetrical position on both sides of the third cavity. In some embodiments, the device also comprises a fluid or buffer solution containing sealed part that can be poked; the sealed part is located between the second and third cavities. Fluid or buffer solution mainly aims to process fluid specimens, which is provided with such functions as dilution, elution, extraction and removal of impurities contained in the fluid specimens. The sealed part can be poked by the flake projection on the outer wall of the third cavity.

In some further embodiments, the sealed part that can be poked is located in the first cavity; the slot entering the first cavity can poke the sealed part to release fluid inside it; such fluid will flow into the second cavity directly or mixed with fluid on the carrier for elution of fluid specimens on the carrier; after that, it will flow into the second cavity in together with fluid specimens.

In some particular embodiments, the first cavity is provided with a third position in the second cavity; when the first cavity rotates from second position to third position, its original space is to be recovered; whereas fluid will flow into the first cavity from the second one; when the first cavity rotates from third position to second position, its space is to be reduced; whereas fluid will flow into the second cavity from the first one.

In some preferred embodiments, when the first cavity rotates from first position or third position to second position or fourth position, two slots will move into the first cavity to reduce its space, and extrude the carrier inside the first cavity to make the fluid flow into the second cavity from the first one.

In a more particular embodiment, when the first cavity rotates from second position to first position or shifts from position 4 to third position, the carrier will make the two slots move out of the first cavity to recover original space of the first cavity (the volume is the same as that at first position), and make the fluid flow into the first cavity from the second one once again.

In still a particular embodiment, the first cavity is also provided with a position 4 inside the second cavity; when the first cavity rotates from first position or 3 to position 4, its space is to be reduced to make the fluid flow into the second cavity from the first one.

In still a particular embodiment, when the first cavity rotates from position 4 to first position or 3, its original space is to be recovered to make the fluid flow into the first cavity from the second one.

In some particular embodiments, when the first cavity rotates from first position or 3 to second position or 4, the flake projection will poke the sealed part between the second and third cavities.

In some further embodiments, the device also comprises a testing cavity containing a testing element; the testing cavity is interconnected with the second cavity.

According to this invention, to ensure relative movement of the first cavity in the second one, the moving element between the first and second cavity, such as moving slot is forced to enter or leave the first cavity to change the volume of the first cavity; variation to the volume can make the fluid inside the first cavity, such as fluid specimens, flow into the second cavity directly or indirectly from the first cavity. In some embodiments, the movement is represented by rotation. Setting of such mutual movement mode aims to change the position of the moving element in the first cavity when it is located at first position, and he first cavity is at second position. For instance, the moving element should be adjacent to or penetrated into the first cavity. For instance, the length of link line at the first and second two points on the inner wall of the second cavity is a and b respectively; a is longer than b; whereas the sum of moving element length and the distance between each moving element is c, which is longer than b. In this way, when the moving element moves from any other position to the shorter link line, the distance between each moving element is to be shortened due to the fact that the length and distance of the moving element exceed the shorter link line on the second cavity; the carrier is to be compressed once the distance is shortened. In some preferred embodiments, the moving element is to be located on the longer link line, namely link line a between the first two points inside the second cavity when it is at first position; the moving element is to be located on the length b between the second two points inside the second cavity when it is at second position. In addition to setting of irregular profile for the second cavity, it is applicable to provide a projection or projected part on the inner wall of the second cavity to change the position of the moving element, and ensure varied linking distance between any point on the inner wall of the second cavity; this can ensure shift of moving element and change of its distance. In some preferred embodiments, moving element is to be moved or transferred simultaneously with the shift of the first cavity; for instance, moving element can be incorporated into the first cavity.

In some further embodiments, the second cavity is an elliptical cylinder; whereas the first cavity is a cuboid structure; when the first cavity is at first position, the moving element is to be located on the longest distance line of the elliptical cylinder; when the first cavity is at second position, the moving element is to be located on the shortest distance line of the elliptical cylinder.

In a further aspect, some further embodiments of this invention aims to provide a device; when the first cavity moves from first position to 2 in correspondence to the second cavity, the moving element between the first and second cavities is to move while the space or volume of the first cavity will remain unchanged; the moving element in movement will compress the compressible carrier inside the second cavity to make the fluid on it flow into the second cavity.

For instance, a particular embodiment of this invention provides a device, comprising a first cavity and a second cavity; wherein, the first cavity is located inside the second one, and is interconnected with it; a moving element is provided between the first and second cavities; the said first and second cavities are available for relative movement to shorten the distance between each moving element.

In a preferred embodiment, a compressible carrier for used to absorb fluid specimens is provided between each moving element, which is used to compress the carrier once the distance between each moving element is shortened. In some preferred embodiment, partial moving elements are located on the first cavity; the first cavity rotates inside the second cavity to make moving elements shift. Such moving elements are expected to enter the first cavity; in this embodiment, the compressible carrier can be placed inside the first cavity in advance; moving elements entering the first cavity will compress the carrier to make fluid specimens inside it flow out. In some preferred embodiments, the first cavity comprises some openings for moving elements to enter the first cavity. Of course, in some preferred embodiments, compressible carrier absorbed with fluid specimens can be located on the fluid specimen collector; firstly, use carrier to collect fluid specimens, such as saliva; after that, insert the carrier into the first cavity to locate it between each moving element or at the position that can be compressed by moving elements.

For instance, this invention aims to provide a device, comprising a first cavity used to collect compressible carrier with fluid specimens, a second cavity and a moving element between the first and second cavities; wherein, the first cavity is located inside the second one, and is interconnected with it; the first cavity aims to make the moving element rotate inside the second cavity; the moving element rotates to compress the carrier inside the first cavity.

The first cavity is provided with an opening on its wall; one end of the moving element penetrates through the opening into the first cavity; whereas another end is adjacent to the inner wall of the second cavity.

The two moving elements are arranged symmetrically, which are provided with a distance 1 and 2 at first position and 2 respectively; distance 1 is longer than distance 2. When moving elements are at first position, they will be located on the link line between the first two points on the inner wall of the second cavity; when moving elements are at second position; they will be on the link line between the second two points on the inner wall of the second cavity; the distance between the first two points is longer than that between the second two points.

The compressible carrier is located between two moving elements as arranged symmetrically; such device also comprises a collection rod composed of the said carrier for collection of fluid specimens. The said collection rod matches with the first cavity to make it rotate inside the second cavity. Rigidity of moving elements is higher than that of the compressible carrier.

The distance between the two moving element arranged symmetrically is to be shortened to compress the carrier with fluid specimens, and make fluid specimens flow into the second cavity from the carrier when they move from first position to second position.

The said fluid is to enter the second cavity via the opening on the inner wall of the first cavity.

In a further aspect, this invention provides a testing method, comprising a testing device; such test device comprises a second cavity and a first cavity inside the second cavity; the first cavity is used to collect fluid specimens, which rotates in correspondence to the second cavity; such rotation aims to change the volume of the first cavity; variation to the volume aims to make fluid specimens in the first cavity flow into the second cavity. In some preferred embodiments, the testing device comprises a moving element that rotates inside the second cavity, driven by the first cavity; rotation of the moving elements aims to reduce the volume of the first cavity. In a further preferred embodiment, the said fluid specimens are absorbed by the compressible carrier; rotation of the moving element aims to compress the said carrier. In a preferred embodiment, rotation of the moving element aims to compress the said carrier.

Beneficial Effect

The device of this invention is easy for collection, storage and transportation of fluid specimens; furthermore, fluid inside the first cavity can fully flow into the second cavity for adequate and even mixing with the fluid inside the second cavity, especially buffer solution so as to facilitate further tests.

DRAWINGS

FIG. 1 is the vertical diagram for the device of this invention;

FIG. 2 is the sectional view for the device of this invention;

FIG. 3 is the breakdown drawing for the device of this invention;

FIG. 4 is the diagram for the slot, the moving element of the device of this invention;

FIG. 5 is another diagram for the slot, the moving element of the device of this invention;

FIG. 6 is the diagram for the first and third cavities of the device of this invention;

FIG. 7 is the diagram for the collection rod of this invention;

FIG. 8 is the diagram for connection between the second cavity of the device of this invention and testing device;

FIG. 9 is the positioning diagram for the first and second cavities (first position and 3);

FIG. 10 is the status diagram for the device of this invention (first position or 3);

FIG. 11 is the A-A section for the status as shown in FIG. 10;

FIG. 12 is another status diagram for the device of this invention (second position or 4);

FIG. 13 is the A-A section for the status as shown in FIG. 12;

FIG. 14 is the diagram for the embodiment of this invention. FIG. 14A indicates that the first cavity is at first position; whereas the moving element 51 is at the initial position; as indicated in FIG. 14B, the first cavity is at second position; whereas the moving element 51 moves into the first cavity to compress the carrier. Viewing from the FIG, it can be seen that position of the moving element is to be changed accompanied by relative movement due to the setting of different profiles and positions of the second and first cavities; eventually, the moving element will compress the carrier directly to release fluid specimens.

FIG. 15 is a diagram for the embodiment of this invention. FIG. 15A indicates that the first cavity is at first position; whereas the moving element 51 is at the initial position; as indicated in FIG. 15B, the first cavity is at second position; whereas the moving element 51 moves into the first cavity to compress the carrier. Viewing from the FIG, it can be seen that position of the moving element is to be changed accompanied by relative movement despite of the fact that position of the first and second cavities are not changed by the profile of the second cavity; eventually, the moving element will compress the carrier to release fluid specimens.

DESCRIPTION OF DRAWING MARKINGS

The specimen collection and testing device 500, the device of this invention 510, the collection rod 520, the testing device 530, the first cavity 512, the open side wall of the first cavity or opening on the side wall 5121, the side wall of the first cavity 5122, the second cavity 511, the third cavity 513, the slot 515, the slot projection 5151, clamping strip on the slot 5152, the groove 5153 on the slot, the washer 516, the upper cover of the second cavity 517, the gasket at the bottom of the second cavity 518, the buffer solution enclosure 5132, the projection 5131 on the external side of the third cavity, the projection 5133 on the inner wall of the third cavity, the handle 521 on the collection rod, the carrier 522 of the collection rod, the connecting rod 523 between the handle and the carrier, groove 524 on the handle, top plate 531 on the testing device, bottom plate 532 on the testing device, the projection 533 on the testing device at the position corresponding to the device of this invention, the first position 801, the second position 802, the third position 803, the fourth position 804 and the moving element 51.

Preferred Embodiments

Further description of structures involved in this invention or technical terms used is stated as follows.

Specimen

"Specimen" in this invention refers to any substance requiring examination for existence and/or analysis of the concentration of the substance analyzed or definition of one or more specimens for the existence and/or quantity of the substance analyzed or substance requiring qualitative evaluation. Specimen can be fluid specimen. The fluid specimen comprises body fluids, such as blood, serum, plasma, saliva, urine, tear, semen and marrow; fluid specimen can also be aqueous ones, such as seawater, river water or living water, municipal water or industrial water resource, runoff or sewage; it can also be food specimens, such milk and wine. Mucus, semi-solid or solid specimens can be used to produce such specimens as fluid, elution, suspensoid or extract. For instance, throat or genital organ specimen can be fabricated through soaking in the fluid. Specimens can be mixture of fluid, solid and gas or any related mixture, such as cell suspensoid in the diluents or solution. Specimens comprise biological substances, such as cell, microbe, organelle and biological compound. Fluid specimens can be extracted from soil, stool, tissue, organ, biological fluid or natural non-fluid specimens, such as solids, semi solids or high-viscosity substances. For instance, such solid or semi-solid specimens can be mixed with such solutions as diluents. Specimens are available for soaking, freezing and thawing or production of fluid specimens with other extraction methods. Residual particles can be removed with such conventional methods as filtration or sedimentation.

Testing Element

"Testing element" refers to any element available for test. In an embodiment, the testing element is a testing strip. Such testing strip comprises a specifically combined substance pair for immune analysis. The testing strip can be a chemical testing strip for judgment of results through observation of variation to colors or other signals after test. Specimens available for test in this invention include but not limited to body fluid and specimens extracted from biological tissues or body fluid. For instance, saliva, blood, serum, plasma, urine, excrement, spinal fluid, vaginal fluid, mucilage and tissue can be used as specimen. Two or more testing elements can be located in the testing device simultaneously for test of different compositions in specimens.

Collection Rod 520

This invention also provides a collection rod 520. In an embodiment, the collection rod 520 comprises an absorption carrier 522 and a handle 521. The absorption carrier 522 is normally made of medicinal sponge or foamed plastic material. However, the absorption carrier can also be made of many other materials, such as cotton or paper or any other water-absorption material. The absorption carrier is provided with certain elasticity, of which space is to be compressed under external force. When the external force is reduced or eliminated, it may recover to its original profile. The collection rod can be soaked in the solution containing saliva as secreted by the people receiving the test, which can make it easy for collection of saliva from the mouth of the test receiver. The handle is normally rigid, which is favorable for manipulation of the absorption carrier. The handle can be made of common materials in this field, such as plastics, wood, metal or cardboard.

Reference attached to illustrations is an integral part of the following detailed description, which aims to specify particular feasible solutions to this invention. We will not exclude the possibility for this invention to introduce other particular solutions, and change its structure within the specified scope.

As shown in FIG. 14, in an embodiment of this invention, the second cavity 510 comprises a carrier 522 and a moving element 51 in corresponding arrangement; at this point, the moving element is at first position in correspondence to the second cavity; in this case, the carrier is not compressed by the moving element as shown in FIG. 14A. Under such circumstance, the distance H between each moving element and the length (A+B) of the moving element itself are on the axis C of the second cavity. Under the pressure from inner wall of the second cavity, the moving element is to approach the center to compress the carrier, and make fluid specimens flow out when it is rotated in the direction of the arrow. See FIG. 14A. Under such circumstance, the moving element is to be located on the axis D of the second cavity with the length of C over that of D.

Similarly, the moving element as shown in FIG. 15 is on the distance of link line at any point inside the second cavity when it is at first position; in this case, the moving element will not compress the carrier; when the moving element is rotated, it shall shift from the position of longer link line at any point inside the second cavity to the shorter one inside the second cavity. Under such circumstance, the moving element will compress the carrier to release the fluid inside it. Similarly, in aforesaid particular embodiments, the carrier can be inserted later in correspondence to the position of the moving element; furthermore, the carrier and the moving element can also be put into the first cavity; make some opening on the wall of the first cavity to insert one end of the moving element into the first cavity, and insert the other end into the second cavity at the position near the inner wall.

Here, the moving element is to be provided with higher rigidity for effective compression of the carrier as compared with it.

In the embodiments as shown in FIGS. 14 and 15, the carrier can be put into the first cavity; the moving element is in direct or indirect contact with the carrier inside the first cavity via the opening. In this way, rotation of the moving element will reduce the volume of the first cavity, and compress the carrier through direct contact so as to enable the carrier absorbed with fluid specimens to extrude it.

Figure 2:
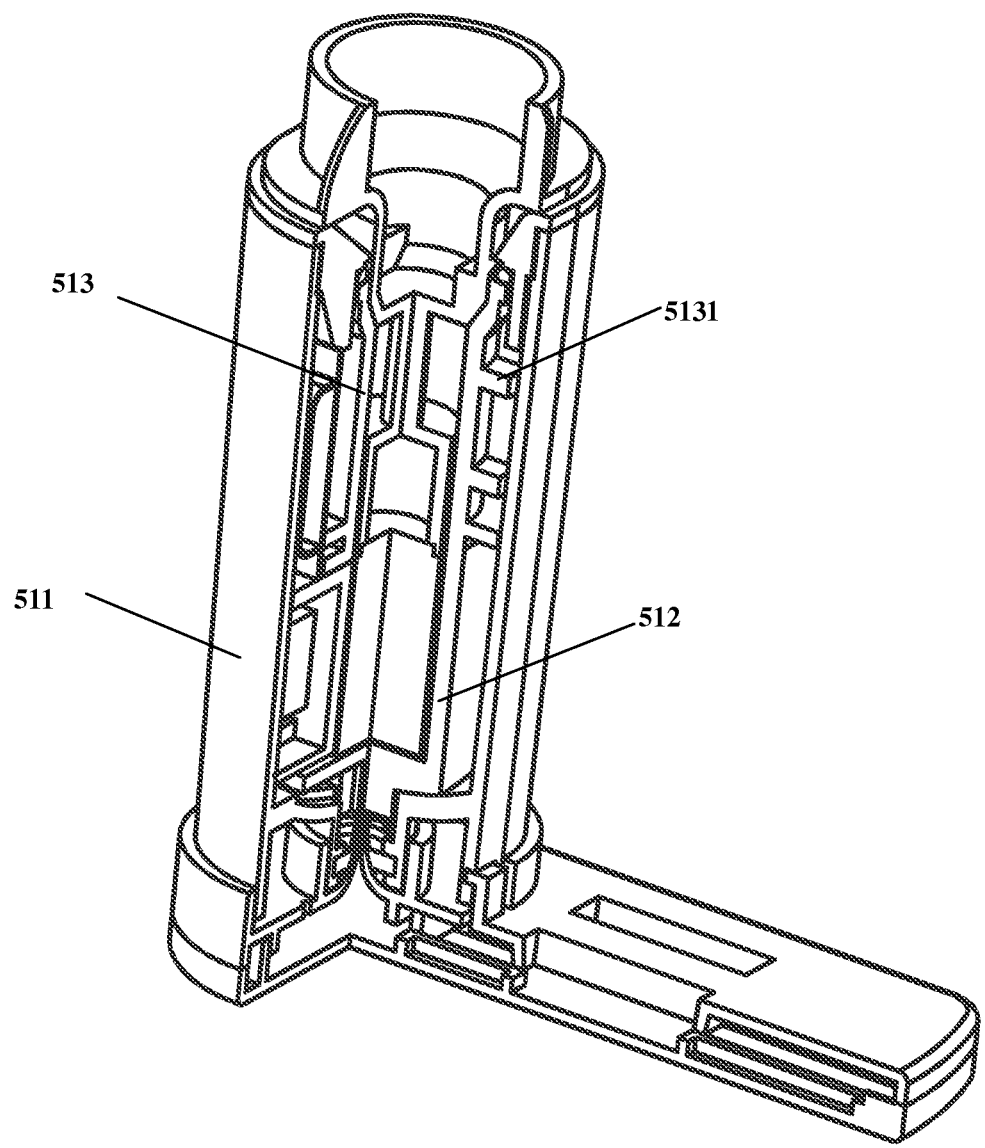
Figure 3:
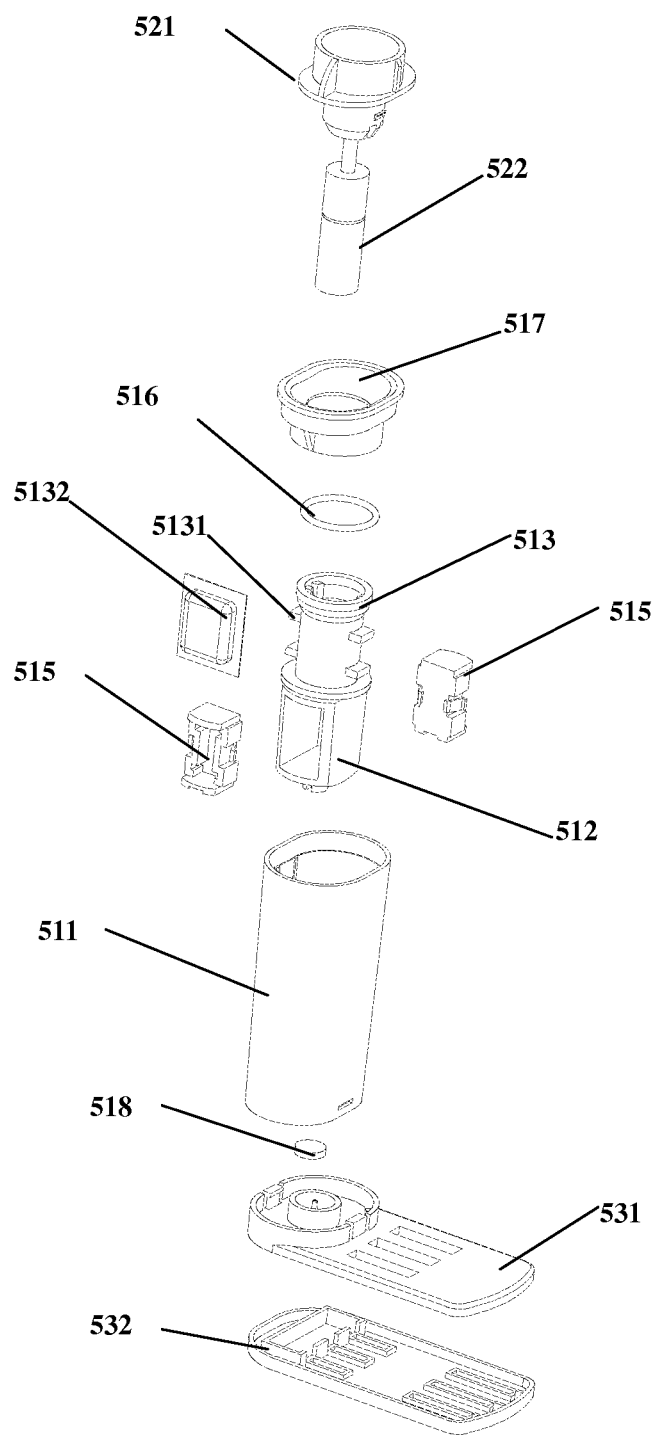
Figure 6:
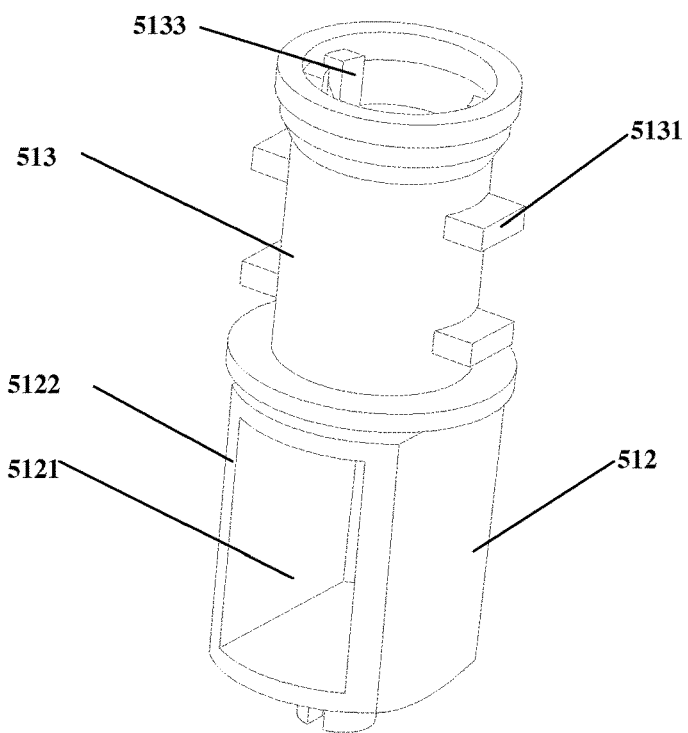

In one of some other embodiments as shown in FIG. 3, the device 510 comprises a first cavity 512 and a second cavity 511; wherein the first cavity 512 is located inside the second cavity 511 as shown in FIG. 2, the sectional view; furthermore, the first cavity 512 is interconnected with the second cavity 511. In a particular embodiment, the two is interconnected with the opening 5121 on the side wall of the first cavity. Profile of the first cavity 512 and the second cavity 511 is not limited on condition that it can enable the second cavity 511 to contain the first cavity 512, and ensure its free rotation inside the second cavity 511. For instance, it can be in cylindrical, cubic, cuboid and conical forms, etc. As shown in FIG. 6, the first cavity 512 is in cuboid structure; among 4 side walls, two symmetrical ones 5121 are open; in other words, no side walls are provided on the two symmetrical sides. The second cavity 511 is an internally hollowed elliptical cylinder; the short radius of such elliptical cylinder slightly exceeds the length and width of the cuboid structure of the first cavity. The first cavity 512 is interconnected with the second cavity 511 via the open side wall 5121 on the first cavity. In a more particular embodiment, the fluid inside the first cavity 512 will flow into the second cavity 511 via the two open side walls 5121 when the first and second cavities are in mutual rotation; alternatively, the fluid inside the second cavity 511 will flow into the first cavity 512 via the two side walls 5121.

Figure 9:
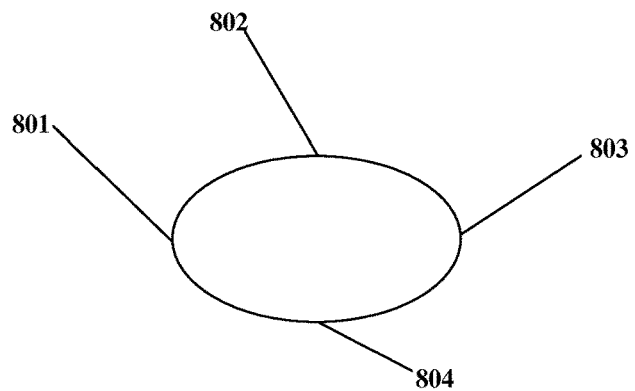

The first cavity 512 is available for free rotation inside the second cavity 511; furthermore, flow inside the two cavities in mutual rotation is also available for mutual flowing. In some particular embodiments, the first cavity 512 is provided with the first position 801 and the second position 802 corresponding to the second cavity 511 when it rotates inside the second cavity 511; see FIG. 9. When the initial position of the first and second cavities is first position or the first cavity is located at the first position 801 inside the second cavity, the initial status can be defined. When the first cavity 512 rotates to the second position 802 from the first position 801, space of the first cavity 512 is to be reduced to make the fluid flow into the second cavity 511 from the first cavity 512. As the space of the first cavity 512 is reduced, fluid inside is also to be decreased; therefore, fluid in the original first cavity 512 is to flow into the second cavity 511 from the open side wall 5121. When the first cavity 512 rotates to the first position 801, namely the initial position, from the second position 802, space of the first cavity 512 is to be recovered. In this case, fluid inside the second cavity 511 will flow into the first cavity 512 from the open side wall 5121. In this way, circulation of fluid inside the first and second cavities can be realized. In some further embodiments, the first cavity 512 also comprises a third position 803 and a fourth position 804 as shown in FIG. 9 in the second cavity 511; the third position 803 is behind the second position 802; whereas the fourth position 804 is located behind the third position 803; the fourth position 804 is followed by the first position 801. In some particular embodiments, when the first cavity 512 rotates to the third position 803 from the second position 802, space of the first cavity 512 is to be recovered; whereas fluid will low into the first cavity 512 from the second cavity 511; when the first cavity 512 rotates to the second position 802 from the third position 803, space of the first cavity 512 is to be reduced; whereas fluid will flow into the second cavity 511 from the first cavity 512. When the first cavity 512 rotates from the first position 801 or the third position 803 to the fourth position 804, space of the first cavity 512 is to be reduced; whereas fluid will flow into the second cavity 511 from the first cavity 812.

Figure 4:
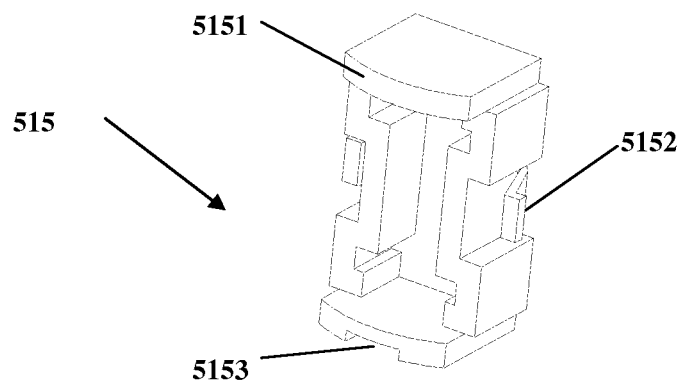
Figure 5:
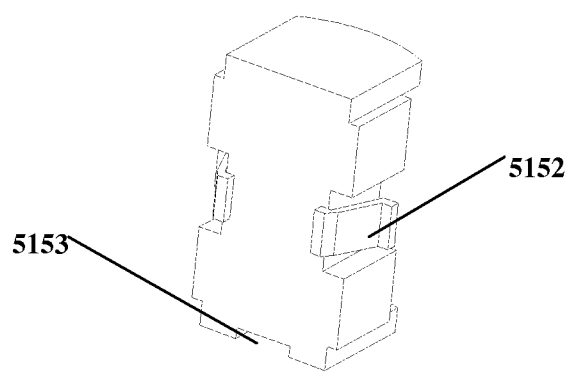

In some embodiments, two corresponding moving elements are provided on the open side wall 5121 of the first cavity, such as moving slots 515; the two slots are movable; height of the slots 515 is the same as that of the inner side wall 5121; at initial status, the slots 515 are located on the edge of side wall 5122 with partial section located inside the second cavity 511. As shown in FIGS. 4 and 5, the slot 515 is provided with a clamping strip 5152 matching with the side wall 5122 of the first cavity; the clamping strip 5152 are in flexible connection with the slot 515; in this way, the clamping strip 5152 is to be provided with a movement scope on the slot 515; the end of the clamping strip 5152 is provided with a bent part that aims to fix the slot 515 to the side wall 5122 on the first cavity at the initial position. The slot 515 is provided with a groove 5153 at its bottom; the groove 5153 aims to ensure the circulation of fluid inside the first cavity 512 and the second cavity 511. Furthermore, the slot 515 is also provided with a projection 5151 on its top; when the slot 515 is at the initial position 801 on the first cavity 512, the projection 5151 is to be located inside the second cavity 511. In some embodiments, when the first cavity 512 and the second cavity 511 are in rotation, the slot 515 inside the first cavity 512 will rotate with the first cavity 512; when it rotates to the designated position, the projection 5151 on the slot 515 will be in contact with the inner wall of the second cavity 511; if the rotation continuous, the projection 5151 is to be compressed by the inner wall of the second cavity 511; as the side wall of the second cavity 511 is fixed, and the slot 515 is movable inside the first cavity 512, the whole clamping strip 5152 on the slot 515 containing the projection 5151 is to be compressed inward; as a result of it, the bent part is to be disconnected from the side wall 5122 of the first cavity 512; whereas the slot 515 is to shift into the first cavity 512 to reduce its space through extrusion. When the first cavity 512 is located at the second position 802 or the fourth position 804 on the second cavity 511, projection 5151 of the slot is to be located at the short radius of the second cavity 511 of the elliptical cylinder; in such case, the slot 515 is located at the innermost position inside the first cavity 512. In a particular embodiment, the two slots 515 occupy the whole space inside the first cavity 512; in other words, the two slots are in contact with each other. In this case, fluid inside the first cavity 512 is to flow into the second cavity 511 from via the open side wall 5121 of the first cavity and groove 5153. After that, when the first cavity 512 rotates again in correspondence to the second cavity 511, the projection 5151 on the slot will shift from the short radius on the elliptical cylinder to the long radius due to the elliptical structure; in other words, the projection 5151 is to be released gradually by the inner wall of the second cavity; whereas slot 515 is to be ejected from the first cavity 512. When the first cavity 512 rotates to the third position 803 or the first position 801 where the slot 515 is corresponding to the long radius of the elliptical cylinder on the second cavity 511, the slot 515 is to be fully ejected from the first cavity 512; the clamping strip 5152 on the slot will also recover its elasticity automatically; whereas its bent part is to be clamped to the inner wall 5122 of the first cavity 512 to recover the original position of the slot 515.

In a particular embodiment, the first cavity 512 also comprises a third cavity 513; the third cavity 513 is connected with the first cavity 512; furthermore, the first cavity 512 is interconnected with the inner part of the third cavity 513 to make sure that the collection rod 520 can enter into the first cavity 512 from the third cavity 513. In a further particular embodiment as shown in FIG. 6, the third cavity 513 is a hollowed cylinder fixed to the first cavity 512. The third cavity is provided with a flake projection 5131 on its outer wall; in still a further embodiment, the projection 5131 on the third cavity is corresponding to the upper part of the closed side wall 5122 on the first cavity as shown in FIG. 6. In an embodiment, the third cavity 513 is also located inside the second cavity 512; furthermore, a sealed part 5132 is provided in the space as formed by the third cavity 513 and the second cavity 511. One side of this sealed part 5132 can be composed of aluminum foil that can be poked. The fluid reagent is enclosed in the sealed part. In a particular embodiment, the fluid reagent is buffer solution. When the first cavity 512 rotates inside the second cavity 511, the third cavity 513 as fixed to the first cavity 512 is to rotate inside the second cavity 511 with the first cavity 512; when the third cavity 513 rotates from the first position 801 to the second position 802 on the second cavity 511, the flake projection 5131 on the third cavity will contact, extrude and poke the aluminum foil on the sealed part 5132 to make the buffer solution inside it flow into the second cavity 511 during rotation. In a further embodiment, the fluid inside the first cavity 512 will flow into the second cavity 511 at the same time due to the extrusion by the slot; the fluid is to be mixed with the buffer solution inside the second cavity 511.

Figure 7:
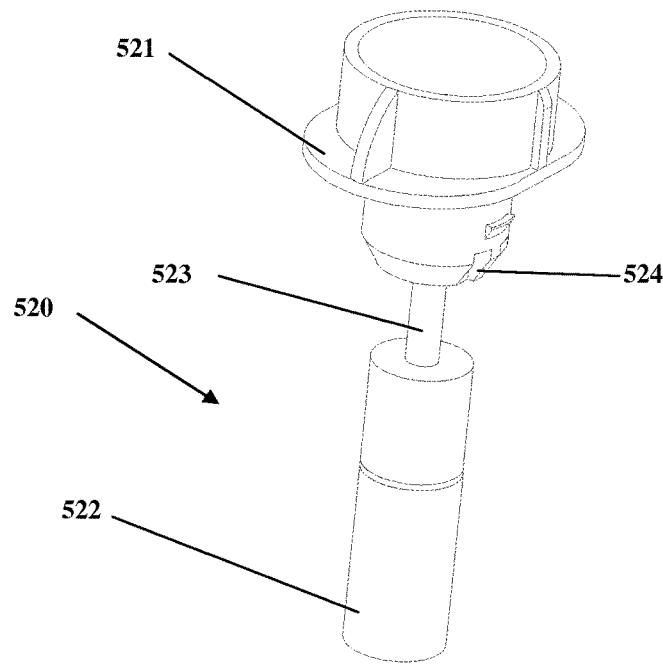

In some embodiments, the device also comprises a collection rod 520 as shown in FIG. 7; the collection rod 520 comprises a handle 521, an absorption carrier for collection of specimens and a connecting rod 523 used to connect the two. In practical operation, the carrier 522 of the collection rod is to be put into the oral cavity of test receiver; after that, put the collection rod 520 fully absorbed with specimens into the third cavity 513, and eventually locate the whole carrier 522 of the collection rod in the first cavity 512. In some further particular embodiments, the collection rod 520 is in closely integrated with the third cavity 513; furthermore, collection rod 520, the third cavity 513 and the first cavity 512 rotate inside the second cavity 511. As shown in FIGS. 6 and 7, the handle 521 of the collection rod is provided with a groove 524; whereas a compatible projection 5133 is provided with on the inner wall of the third cavity 513; when the collection rod is inserted into the third cavity 513 and the first cavity 512, the groove 524 is to be interlocked with the projection 5133 to fix the collection rod 520 inside the third cavity 513 and the first cavity 512. When the first cavity 512 rotates from the first position 801 or the third position 803 to the second position 802, or the fourth position 804 or the collection rod 520, the third cavity 513 and the first cavity 512 rotate from the first position 801 or the third position 803 to the second position 802 or the fourth position 804, the two slots 515 inside the first cavity 512 will moves into the first cavity 512 under the extrusion of the second cavity 511 to narrow its space and extrude the carrier 522 inside the first cavity 512; under such circumstance, the carrier 522 carries fluid specimens, such as saliva; when the carrier 522 is extruded and compressed, the saliva inside it will flow into the second cavity 511 via the open side wall 5121 on the first cavity and the groove 5153 on the slot. At the same time, the flake projection 5131 on the outer wall of the third cavity is to poke the sealed part 5132 between the second cavity 511 and the third cavity 512 when the third cavity 513 is rotating; buffer solution inside the sealed part will flow into the second cavity 511. Buffer solution is to be mixed with the salvia in the second cavity. To ensure full mixing of the two, collection rod 520, the third cavity 513 and the first cavity 512 are to be rotated from the second position 802 or the fourth position 804 to the first position 801 or the third position 803 again; under such circumstance, pressure as imposed by the side wall of the second cavity 511 on the slot 515 is to be eliminated to stop extruding the carrier 522 of the collection rod; as the elasticity of the carrier 522 is recovered, the carrier 522 will make the two slots 515 move out of the first cavity 512; eventually, the space of the third cavity 512 is to be recovered; furthermore, the mixed fluid inside the second cavity 511 is to be absorbed by the carrier 522, which will flow from the second cavity 511 into the first cavity 512.

Figure 8:
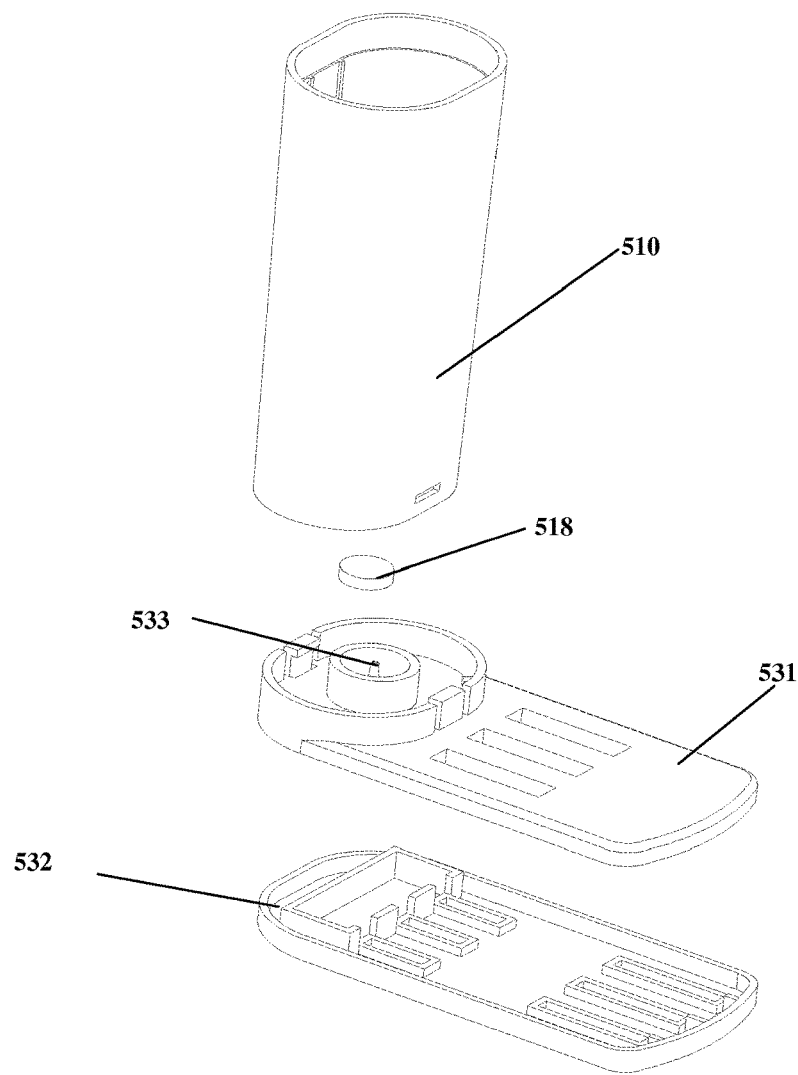

In a further embodiment, the device comprises a testing cavity 530 as shown in FIGS. 1, 3 and 8. The testing cavity 530 comprises an upper cavity 531 and a lower cavity 532; it is applicable to place a testing element between the two cavities. The upper cavity 531 is provided with a projection 533 matching with the bottom of the second cavity 511 to ensure the fluid inside it to flow into the testing cavity 530. Particularly speaking, the second cavity 511 is provided with a hole as sealed by the gasket 518. The projection 533 on the testing cavity 530 can poke the gasket 518. Furthermore, the projection 533 is corresponding to the specimen collection area of the testing element inside the testing cavity 530. The projection 533 is hollowed, of which the end is provided with a hole; when the projection 533 is inserted into the bottom of the second cavity 511, the mixed fluid inside the second cavity 511 will flow into the hollowed projection 533 via the hole on it; after that, it will further flow into the testing cavity 530 corresponding to the projection 533.

Figure 11:
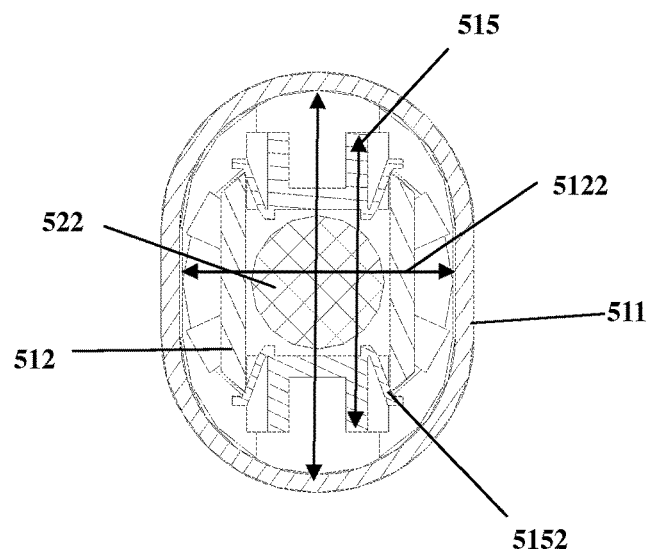

The whole operation process for the device 500 of this invention is stated as follows. As shown in FIGS. 1, 2 and 3, the first cavity 512 of the cuboid structure is fixed to the third cavity 513 of the cylinder; the two slots 515 are located on the open side wall 5121 of the first cavity; the two clamping strips 5152 on each slot 515 are clamped on the side wall 5122 of the first cavity at the bent part as shown in FIG. 11, the sectional view. The projection 5151 of the slot is located on the top of the open side wall 5121; whereas the slot groove 5153 is located at the bottom of the open side wall 5121. Bottom of the first cavity 512 is located at the bottom of the second cavity 511; bottom of the second cavity 511 is provided with trumpet shaped groove to facilitate rotation of the first cavity 512 inside it. The trumpet groove is provided with a circular hole equipped with a rubber washer 518; diameter of the washer 518 is equal to or slightly bigger than that of the circular hole for the purpose of sealing up the circular hole. The third cavity 513 is provided with a symmetrical flake projection 5131 as shown in FIGS. 3 and 6; there are altogether 4 flake projections 5131 as equally distributed on both sides; the projections 5131 are located above the side wall 5122 of the first cavity. A sealing washer 516 is fixed to the mouth of the third cavity 513; the washer 516 is provided with an upper cover 517 sealed up with the second cavity 511; in this way, the third cavity 513 and the first cavity 512 are to be enclosed inside the second cavity 511 to prevent fluid inside from overflowing. Of course, a sealed part 5132 containing buffer solution is also provided between the second cavity 511 and the third cavity 513; the sealed part 5132 is located on one side of the third cavity 513 not provided with a flake projection; in other words, it is located at the long radius of the second cavity 511. Furthermore, one side of the sealed part 5132 that can poke the aluminum foil is just opposite to the third cavity 513. As shown in FIGS. 3 and 7, the handle 521 of the collection rod 520 is provided with an elliptical profile matching with the upper cover 517 of the second cavity.

Figure 10:
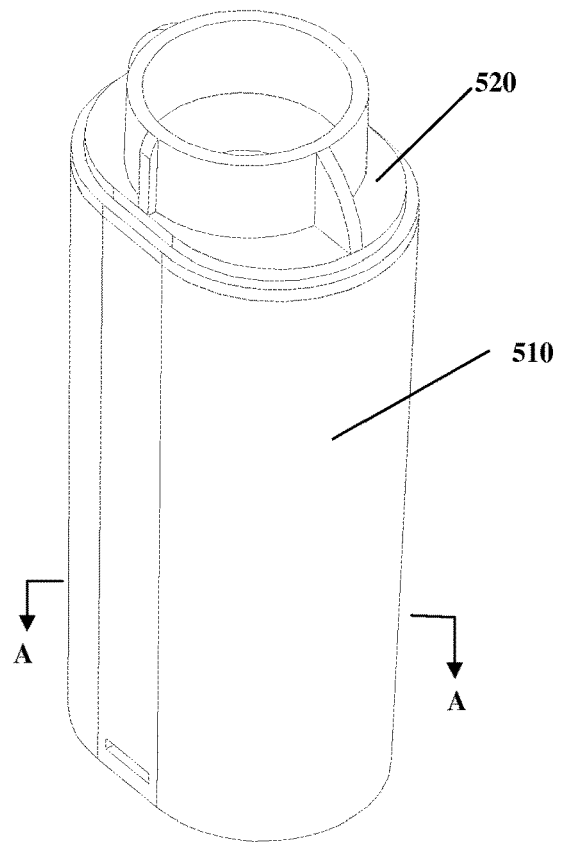

Firstly, the operator is requested to hold the handle 521 of the collection rod, and put the carrier 522 of the collection rod into the mouth of the person receiving the test, and wait for 1-5 minutes to make the absorption carrier to fully absorb the saliva specimen. After that, insert the collection rod 520 into the device of this invention with its end oriented downwards; under such circumstance, the carrier 522 of the collection rod is located between the two slots 515 of the first cavity 512 as shown in FIG. 11. The groove 524 on the connecting rod 523 of the collection rod is interlocked with the projection 5133 inside the third cavity 513 to link up the collection rod 520, the third cavity 513 and the first cavity 512. Furthermore, handle 521 of the collection rod is fully integrated with the upper cover 517 of the second cavity as shown in FIG. 10. At this point, the collection rod 520, the third cavity 513 and the first cavity 512 are at the first position 801 of the second cavity 511, namely the initial position; its status is as shown in FIGS. 10 and 11.

Figure 12:
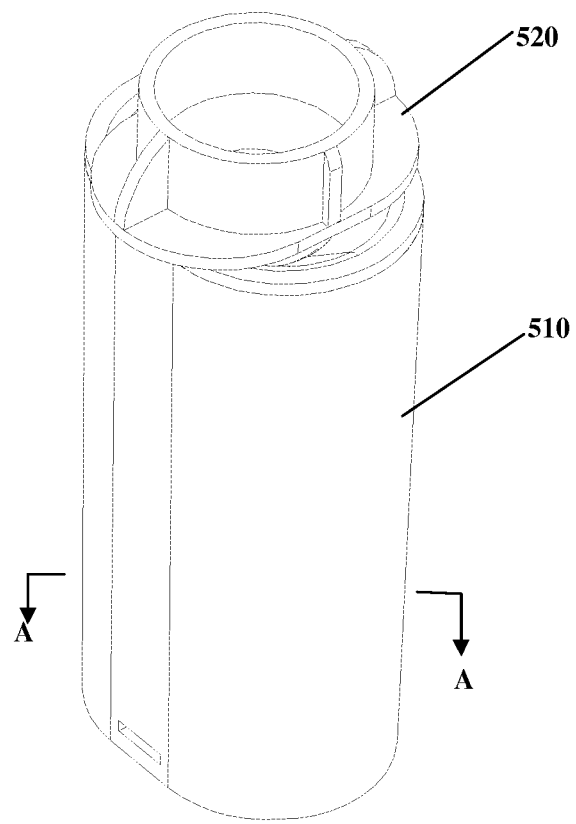
Figure 13:
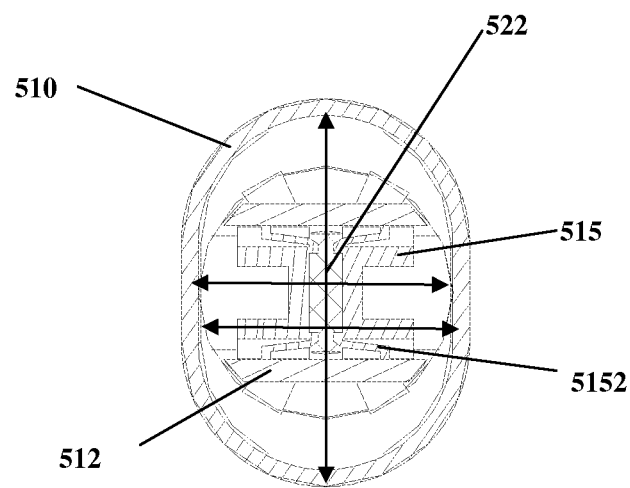

After that, press the handle 521 of the collection rod 520 as shown in FIG. 9, and make the collection rod 520 rotate from the first position 801 to the second position 802. The projection 5151 of the slot 515 is to be in contact with the inner wall of the second cavity 511 under its extrusion in the process of rotation; when the pressure is up to certain degree, the clamping strip 5152 on the slot 515 is to be under extrusion and compression; after that, the slot 515 will move into the first cavity 512. The slot 515 moving inwards will press the absorption carrier 522 of the collection rod 520 inside the first cavity 512. The saliva specimen on the carrier 522 is to be discharged under extrusion, which will flow into the first cavity 512 before flowing into the second cavity 511 through the open side wall 5121 of the first cavity and the groove of the slot 5153. When the collection rod 520 rotates to the second position 802 on the second cavity 511 as shown in FIG. 12, handle 521 of the collection rod is to be vertical to the upper cover 517 of the second cavity 511. At this point, the slot 515 located at the shortest part (short radius) of the second cavity 511 is to be under the maximum pressure; whereas the slot 515 will fully enter the first cavity 512 to compress the carrier 522 to the minimum. Eventually, the saliva discharged from the carrier 522 will flow into the second cavity 511. As shown in FIG. 13, the sectional view, clamping strip 5152 is to be located inside the slot 515; the two slots 515 will be fully located into the first cavity 512. Meanwhile, when the collection rod 520 rotates to the second position 802 on the second cavity 511, the third cavity 513 will rotate inside the second cavity 511 simultaneously; as a result of it, the sealed part 5132 at the long radius of the second cavity 511 will be in contact with the flake projection 5131 on the third cavity 513; as the space is so limited, the flake projection 5131 will extrude and poke the aluminum foil of the sealed part 5132. Buffer solution inside the sealed part 5132 will flow out from the opening of the aluminum foil before further flowing into the second cavity 511 for mixing with the saliva specimen from the first cavity 512.

To ensure adequate mixing of saliva specimen and buffer solution, the collection rod 520 is to be rotated from the second position 802 to the third position 803. At this point, status of collection rod 520 and the second cavity 511 is as shown in FIG. 10. In the process of rotation, the slot 515 inside the first cavity 512 will move away from the short radius of the second cavity 511, and shift to the long radius; meanwhile, pressure as imposed by the inner wall of the second cavity 511 is to be reduced gradually; whereas the projection of on the slot is to be release gradually; correspondingly, pressure as imposed by the slot 515 on the absorption carrier 522 will also witness a decrease. Once the pressure is release, carrier 522 will be recovered to its original size owing to its own elasticity. Once the carrier is recovered to original profile, the slot 515 will move towards the external part of the first cavity 512 under compression; when the slot moves to the side wall 5122 of the first cavity at the bent part of the clamping strip 5152, the clamping strip 5152 will recover its elasticity; after that, it is to be ejected with the bent part being pressed on the side wall 5122 to fix the slot 515 as shown in FIG. 11. At this point, the mixed fluid inside the second cavity 511 will be at a higher level above the bottom of the first cavity 512; the underlying cause for the carrier to recover its original profile is due to its extremely high absorption; therefore, the mixed fluid inside the second cavity 511 will flow into the first cavity 512 through the open side wall 5121 of the first cavity and the groove 5153 on the slot, which is to be absorbed by the carrier 522. The mixed fluid as absorbed by the carrier 522 will subject to adequate mixing in the carrier 522.

Rotate the collection cavity 520 again to shift it from existing third position 803 to the fourth position 804; under such circumstance, similar to the previous collection rod 520 as rotated from the first position 801 to the second position 802, the slot 515 on the first cavity 512 is to be fully shifted into the first cavity 512 to extrude the carrier 522, and make the mixed fluid on it flow into the second cavity 511.

In some further particular embodiments, it is applicable to connect the device of this invention to a testing cavity 530 for test. Particularly speaking, align the gasket 518 at the bottom of the second cavity 511 with the projection 533 in the specimen collection area on the testing cavity 530. The projection 533 is hollowed with the hollowed part interconnected with the specimen collection area on the testing element inside the testing cavity 530. The projection 533 is provided with a small hole on its top for interconnection with its hollowed part of the projection 533. The projection 533 on the testing cavity will poke the gasket 518 on the second cavity 511 to enter it; the adequately mixed fluid inside the second cavity 511 will flow into the testing element of the testing cavity 530 from the small hole on the projection 533 for relevant tests by the testing element.

The invention claimed is:

1. A device for the collection and testing of fluid specimens, comprising a first cavity and a second cavity; wherein, the first cavity is located inside the second cavity; furthermore, the first and second cavities are interconnected; the said first cavity is available for mutual rotation with the second cavity to facilitate fluid to flow between them; the first cavity movable to a first position and to a second position inside the second cavity, characterized in that volume of the first cavity rotated to the second position is to be reduced to facilitate fluid inside the first cavity to flow into the second cavity.

2. The device according to claim 1, characterized in that the first cavity is interconnected with the second cavity via a side wall of an opening of the first cavity; the said first cavity comprises two symmetrical moving elements; when the first cavity rotates to the second position, the moving elements driven by the first cavity will enter the first cavity via the opening to reduce the volume of the first cavity.

3. The device according to claim 2, characterized in that each moving element comprises a projection matching the second cavity; an inner wall of the second cavity will push the projection to make the moving element move into the first cavity when the first and second cavities are rotating.

4. The device according to claim 2, characterized in that each moving element comprises a passage enabling fluid to flow into the second cavity from the first cavity.

5. The device according to claim 2, characterized in that the first cavity is configured to collect a compressed carrier carrying fluid specimens; the said carrier is to be compressed when the moving element enters the first cavity.

6. The device according to claim 5, further comprising a collection rod composed of the said compressed carrier.

7. The device according to claim 6, wherein said collection rod is in accommodation with the first cavity to make it rotate inside the second cavity.

8. The device according to claim 2, the device further comprises a sealed part containing buffer solution; the sealed part is located inside the first cavity, when the moving element enters the first cavity, said sealed part will be poked.

9. The device according to claim 2, the device further comprises a third cavity fixed to the first cavity; the sealed part is located between the second and third cavities; an outer wall of the third cavity comprises a projected poking element.

10. The device according to claim 9, the poking element configured to poke the sealed part between the second and third cavities when the first cavity shifts from the first position to the second position.

11. The device according to claim 2, the device further comprises a testing cavity for collection of testing elements; the testing cavity is in communication with the phase fluid in the second cavity.

12. The device according to claim 2, characterized in that a length of link line at two points inside the second cavity is a and the length of a link line at two other points inside the second cavity is b; a is longer than b; whereas the sum of moving element length and the distance between each moving element is c, which is longer than b.

13. The device according to claim 12, characterized in that the moving element at the first position is located on a length a of link lines at any two points inside the second cavity; whereas the moving element at the second position is located on the length b of link lines at any two points inside the second cavity.

14. The device according to claim 2, wherein the second cavity is an elliptical cylinder; whereas the first cavity is a cuboid structure; when the first cavity is at first position, the moving element will be on the longest distance line of the elliptical cylinder; when the first cavity is at second position, the moving element will be on the shortest distance line of the elliptical cylinder.

15. The device according to claim 5, wherein fluid specimens comprise saliva, blood or sweat.

16. A testing method, comprising: providing a testing device comprising a second cavity and a first cavity inside it; the first cavity is configured to collect fluid specimens; wherein said testing device comprises a moving element, driven by the first cavity; the moving element will rotate inside the second cavity to reduce the volume of the first cavity; rotating the first cavity in correspondence to the second cavity to change the volume of the first cavity and wherein volume variation will make fluid specimens flow into the second cavity from the first cavity.

17. The method according to claim 16, wherein said fluid specimens are affixed to a compressible carrier.

18. The method according to claim 16, wherein said carrier is compressed through rotation of the moving element.

* * * * *